(12) United States Patent
Mohamadi

(10) Patent No.: US 11,344,215 B2
(45) Date of Patent: May 31, 2022

(54) HANDHELD AND PORTABLE SCANNERS FOR MILLIMETER WAVE MAMMOGRAPHY AND INSTANT MAMMOGRAPHY IMAGING

(71) Applicant: Farrokh Mohamadi, Irvine, CA (US)

(72) Inventor: Farrokh Mohamadi, Irvine, CA (US)

( * ) Notice: Subject to any disclaimer, the term of this patent is extended or adjusted under 35 U.S.C. 154(b) by 615 days.

(21) Appl. No.: 14/841,275

(22) Filed: Aug. 31, 2015

(65) Prior Publication Data
US 2016/0066811 A1 Mar. 10, 2016

Related U.S. Application Data

(60) Provisional application No. 62/046,826, filed on Sep. 5, 2014.

(51) Int. Cl.
*A61B 5/0507* (2021.01)
*A61B 5/00* (2006.01)

(52) U.S. Cl.
CPC .......... *A61B 5/0507* (2013.01); *A61B 5/4312* (2013.01); *A61B 5/7246* (2013.01); *A61B 2560/0431* (2013.01); *A61B 2576/02* (2013.01)

(58) Field of Classification Search
CPC .................................................. A61B 5/0507
See application file for complete search history.

(56) References Cited

U.S. PATENT DOCUMENTS

| | | | |
|---|---|---|---|
| 7,830,989 B2 | 11/2010 | Mohamadi | |
| 7,839,283 B2 | 11/2010 | Mohamadi | |
| 7,884,757 B2 | 2/2011 | Mohamadi et al. | |
| 7,884,776 B2 | 2/2011 | Mohamadi | |
| 8,154,339 B2 | 4/2012 | Zolghadri et al. | |
| 8,237,604 B2 | 8/2012 | Mohamadi et al. | |
| 8,766,743 B2 | 7/2014 | Mohamadi et al. | |

(Continued)

OTHER PUBLICATIONS

J. Sachs et al, Ultra-Wideband Pseudo-Noise Sensors and their Application in Medical Engineering, Non-Destructive Testing and for Search and Rescue, Sep. 7-10, 2009, Faculty of Electrical Engineering and Information Technology, 54. IWK.*

(Continued)

*Primary Examiner* — Rochelle D Turchen
(74) *Attorney, Agent, or Firm* — Haynes and Boone, LLP

(57) ABSTRACT

Methods and systems provide a non-ionizing alternative to conventional mammography X-ray techniques, which expose patients to ionizing radiation, for breast cancer tumor detection, using a miniaturized (wafer scale) array of ultra wide band (UWB) radio frequency (RF) sensors operating at 60 GHz (non-ionizing—no X-ray type accumulative radiations) that have capability to use both linear and polarized sensors, tomography, and suppression of scattering for improved imaging. Coding techniques provide significant processing gain that is essential for the large attenuation of transmitted signals in breast tissue operating at these high frequencies. The increased bandwidth of UWB RF detection provides better depth resolution of breast and body tissue. Using polarization improves detection of abnormal tissues. An extremely miniaturized (wafer scale) cluster of transmitter and receiver antenna elements improves detection at deeper parts of the breast and can detect cancerous cells in dense breasts often not picked up by mammography.

7 Claims, 13 Drawing Sheets

(56) References Cited

U.S. PATENT DOCUMENTS

| | | | |
|---|---|---|---|
| 2009/0015832 A1* | 1/2009 | Popovic | A61B 5/05 356/342 |
| 2011/0168891 A1* | 7/2011 | van der Weide | G01N 21/3581 250/334 |
| 2013/0307716 A1 | 11/2013 | Mohamadi | |
| 2014/0309522 A1* | 10/2014 | Fullerton | A61B 5/064 600/424 |

OTHER PUBLICATIONS

N. Chahat, M. Zhadobov, and R. Sauleau, "Broadband Tissue-Equivlant Phantom for BAN Applications at Millimeter Waves", IEEE Transactions on Microwave Theory and Techniques, vol. 60, No. 7, pp. 2259-2265, Jul. 2012.

M. Kojima, H. Sasaki, K. Sasaki, T. Sakai, K, Wake, S. Watanabe, Y. Kamimura, A. Hirata, Y. Suzuki, and M. Taki, "Investigation of acute ocular injury threshold by 76GHz band exposure in rabbits", General Assembly and Scientific Symposium, 2011 URSI, Aug. 13-20, 2011.

\* cited by examiner

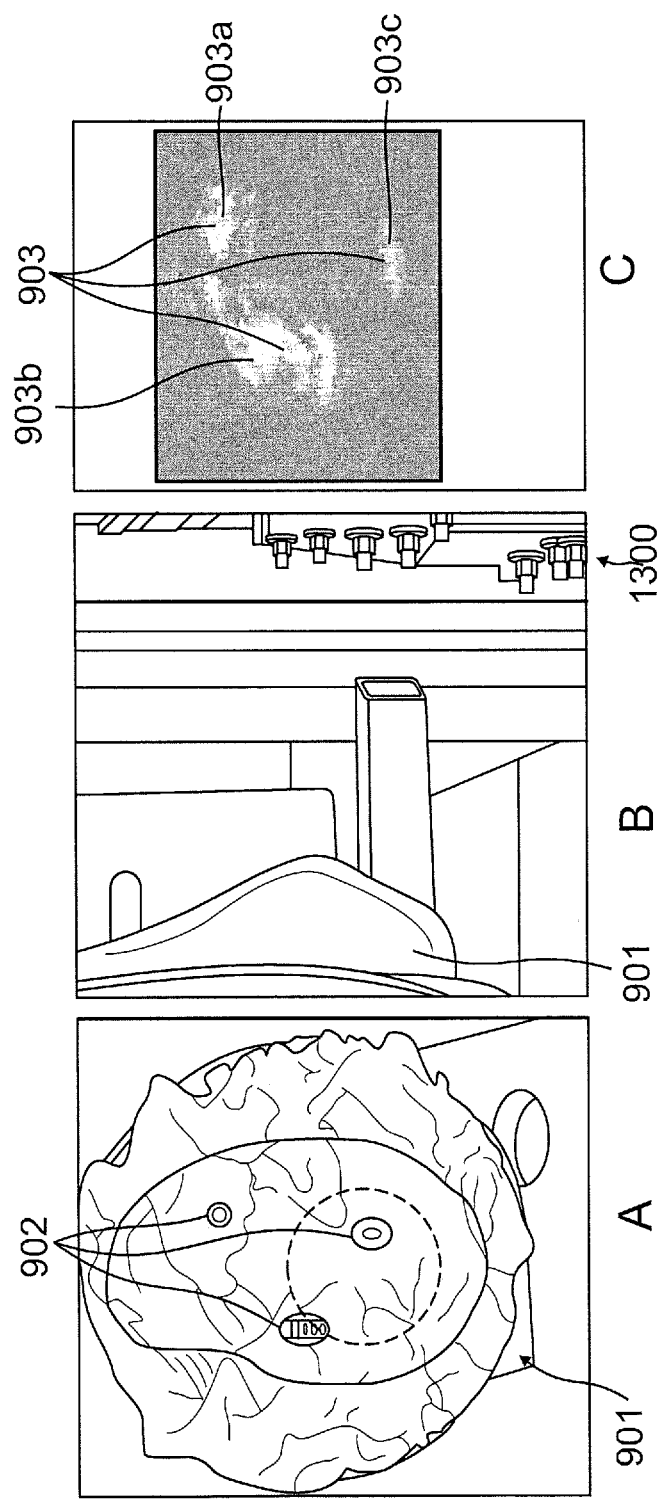

HANDHELD AND PORTABLE SCANNERS FOR MILLIMETER WAVE MAMMOGRAPHY AND INSTANT MAMMOGRAPHY IMAGING

CROSS REFERENCE TO RELATED APPLICATIONS

This application claims the benefit of priority from U.S. Provisional Patent Application No. 62/046,826, filed Sep. 5, 2014, which is incorporated by reference.

BACKGROUND

Field of the Invention

The present invention relates generally to sensor and imaging systems and, more particularly, to ultra wideband sensor systems integrated with wafer scale antenna arrays for tissue imaging and cancer diagnosis in the field of medicine.

Related Art

The incidence of cancer and, more particularly, that of breast cancer, is generally recognized as a serious medical, economical, and human problem. That the financial costs of cancer can be high for both the person with cancer and for society as a whole is illustrated by the following statistics from the National Institutes of Health (NIH), which estimated the 2009 overall annual costs of cancer were as follows: 1) in 2009: new cases of breast cancer: 173,400, deaths from breast cancer 40,000; 2) direct medical costs (total of all health expenditures): $86.6 billion; 3) indirect mortality costs (cost of lost productivity due to premature death): $130 billion. 4) Total cost of items 2) and 3): $216.6 billion.

Mammography, usually employing low energy x-ray radiation for detection of breast cancer, has been used for detection of cancerous tissues. Early detection has generally been credited with saving lives of individuals and devastation of family members, saving women from pain and suffering of cancer and the treatment process of aged cancer, and enabling pursuit of a productive life for women. A number of imaging technologies for mammography exist and have various advantages and disadvantages.

X-ray mammography, which requires patient contact with the scanner and ionizing radiation impact on the patient, may produce 7% false positives, as high as 40% false negatives, and generally requires a bulky (large, not portable) system that is typically expensive. Infrared imaging, which may not require patient contact with the scanner, relies on thermology based on blood vessels (neo-angiogenesis); disadvantages include a resolution greater than 12 millimeters (mm), shallow depths of detection, may produce 19% false positives, and generally requires a moderately expensive system. Elastic-scattering spectroscopy requires contact with the patient, employing an optical probe biopsy; an injection is required, leading to issues with dispersion for imaging. Scintimammography uses injection of a tracer (a radioactive chemical) that gets collected inside a tumor; disadvantages are seen in the use of radioactive material in a lengthy process resulting in resolution of only 9 mm, and generally requires an expensive system. Ultrasound probes can identify various types of lumps, such as liquid-filled cysts and solid masses, but requires contact with the patient, a lengthy process resulting in resolution of 3 mm, a high false positive rate, and typically requires an expensive system. Confocal microwave imaging employs an array of antennas placed around the breast being scanned requiring contact with the patient, resulting in resolution of 3 mm, and generally requires a bulky (large, not portable) system. Positron emission tomography (PET) employs radioactive glucose that is injected into the patient's body, which is then scanned, and can result in higher doses of X-ray radiation (e.g., 20-30 times that of X-ray mammography); and generally requires a bulky and expensive system. Magnetic resonance imaging (MRI) does not require patient contact and may be more suitable for dense breast tissues; but is prone to false positives, and generally requires a bulky and expensive system.

Among these various technologies, there is still room for a technology for early detection of cancer that does not require patient contact or injections, does not expose the patient to unsafe radiation, does not require painful compression of breast tissue such as experienced with conventional X-ray mammography, does not require a high level of skill on the part of the operator to obtain accurate scans while ensuring patient safety, and provides an easily accessible, low cost, portable or handheld, real-time imager that can be used in a primary care physician's office, for example.

BRIEF DESCRIPTION OF THE DRAWINGS

FIG. 9 comprises three perspective views A, B, and C, showing, at A, a plan view of a phantom, or test model of cancerous body tissue; at B, a profile view of the phantom in operational relationship to a scanning sensor of a mammography scanning system; and at C, a display image of radiometry scan of the phantom produced by a mammography scanning system, each in accordance with one embodiment.

Figure 1:
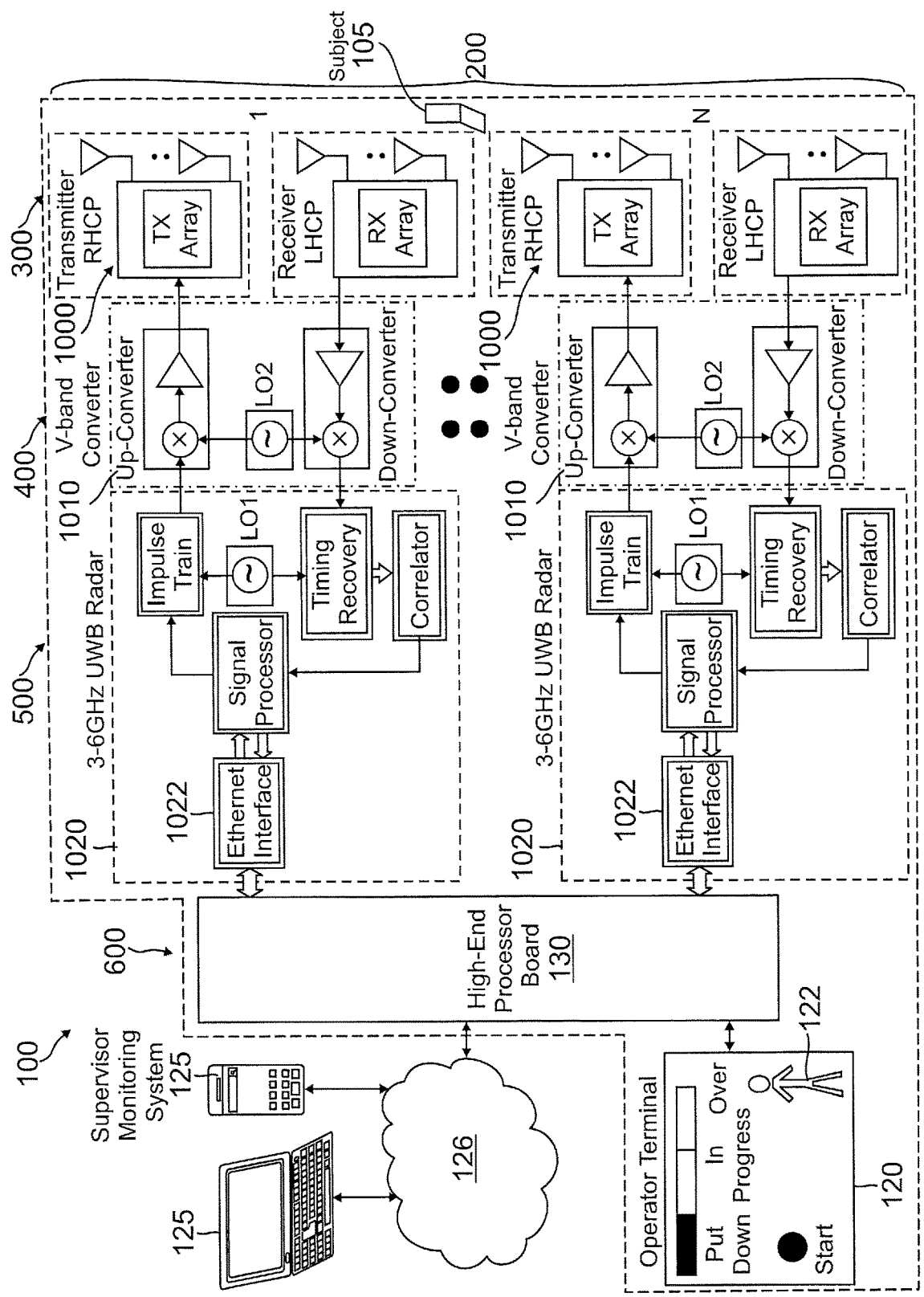
FIG. 1 is a system block diagram showing an example of an implementation for a mammography scanning system using radiometry with wafer scale antenna arrays in accordance with one embodiment.

Embodiments of the present disclosure and their advantages are best understood by referring to the detailed description that follows. It should be appreciated that like reference numerals are used to identify like elements illustrated in one or more of the figures, in which the showings therein are for purposes of illustrating the embodiments and not for purposes of limiting them.

DETAILED DESCRIPTION

Embodiments of the disclosure address the need for a handheld or portable scanning device and real-time imaging that can be used, for example, in a primary care physician's office. Methods and systems are disclosed for ultra wide band (UWB) sensor imaging for medical diagnosis that address the needs for early detection of cancer that does not require patient contact or injections, does not expose the patient to unsafe radiation, does not require painful compression of breast tissue such as experienced with conventional X-ray mammography, does not require a high level of skill on the part of the operator to obtain accurate scans while ensuring patient safety, and provides a low cost, portable or handheld, real-time imager that can be used, for example, in a primary care physician's office. In one embodiment, mobile, handheld, and versatile performance can be obtained in any office or even at home on account of the small volume of the sensor and imaging units which can be on the order of 1/1000 the volume of an MRI or X-ray scanning unit. In one embodiment, an affordable early stage cancer cell detection system can be obtained at only 1/100 the cost for example, of an MRI system. For a primary care physician's office, ergonomic design for ease-of-use by doctors and patients can mean substantial savings of time and availability for diagnostic use without the need for an appointment and ultra-fast scan time (e.g., seconds) to create a diagnostic image.

In addition, a mobile link to doctors from the imaging can be readily implemented in one or more embodiments. For example, in one embodiment, a highly integrated array of sensor clusters rapidly scans the breast area without contact to the patient to detect and display anomalies. An electromechanical scanning system enables the array to "instantly" take a topographic picture of the desired scan area and identify the tissue cluster which has different dielectric properties at the scan frequency range. By scanning a breast and presenting that in a high resolution display unit the image of collected data can be viewed on a network by experts for further decision making.

One or more embodiments provide a non-ionizing alternative to conventional mammography x-ray techniques, which expose patients to ionizing radiation, for breast cancer tumor detection, using a miniaturized (wafer scale) array of UWB radio frequency (RF) sensors operating at 60 GHz (non-ionizing—no X-ray type accumulative radiations) that have the capability to use both linear and polarized sensors, tomography, and suppression of scattering for improved imaging. The increased bandwidth of UWB RF detection provides higher depth resolution of breast and body tissue that improves with increases in bandwidth. In one or more embodiments using polarization enhances detection of abnormal tissues and an extremely miniaturized cluster of transmitter and receiver antenna elements enhances detection at deeper parts of the breast and can detect cancerous cells in dense breasts often not picked up by mammography.

One or more embodiments can employ a version of an ultra wide band (UWB) sensor that can produce very fine beams at the V- or W-bands by using beam forming techniques developed specifically for wafer scale antenna arrays. Due to the high bandwidth (for UWB, in the range of about 1-10 GHz) of very short pulses at the V-band (e.g., about 57-64 GHz range) and W-band (e.g., about 75-110 GHz range), radio waves can penetrate tissue and resolve the tissue anomalies with high-resolution that can be used for depth tomography. For example, a millimeter-wave radio transmitter emits a train of very narrow pulses. The transiently radiated field impinges on tissues in its field of view and returns a reflected portion of that energy to a correlating receiver. Pseudo-random coding (e.g., Hadamard coding) of the pulse train creates a signal and allows the correlating receiver to extract very low energy reflected signals from background noise (e.g., coding gain). This and similar coding techniques provide significant processing gain that is essential to compensate for, and can be used to offset, the large attenuation of transmitted and reflected signals in breast tissue at the high frequencies of V-band and W-band. Furthermore, when multiple sensor scan the breast, the cross channel suppression significantly (20-30 dB) reduces the clutter associated from neighboring channels.

The electro-magnetic properties of materials, in particular the dielectric properties, e.g., relative permittivity ($\varepsilon_r$), exhibit a generally significant contrast in measured value between normal and malignant tissues. Permittivity, being dependent on the frequency of the electric field applied to the material, is usually expressed as a complex number. In general, the dielectric properties (e.g. permittivity) of tumors are much higher than normal tissue, hence, create the capability to detect pronounced reflections with UWB RF interrogation. In research and testing scenarios, measurements of relative permittivity of 10-j9 (conductivity of $\sigma=0.4$ S/m) for samples of human skin and relative permittivity of 50 (conductivity of $\sigma=4.0$ S/m) for malignant breast tissue have been reported at the lower frequency ranges. System 100 can exploit complex permittivity characterizations of healthy and malignant tissue for constructing diagnostic images of healthy and malignant tissue. By measuring the path delay between transmitting and receiving antennas via any desired point in the tissue, it is then possible to extract and time-align all the signals from that point. Repeated for all points in the tissue hundreds of time, the result yields an image in which the distinct dielectric properties of malignant tissue are then presented. To minimize the clutter arising from the air-tissue interface, undesired reflections are removed by cancelling out the systematic errors.

Various embodiments may incorporate teachings from U.S. Pat. No. 8,766,743 issued Jul. 1, 2014, entitled "Wafer Scale Spatial Power Combiner", and U.S. Patent Publication No. 2013/0307716 published Nov. 21, 2013, entitled "Integrated Ultra Wideband, Wafer Scale, RHCP-LHCP Arrays", which are both incorporated by reference.

FIG. 1 is a system block diagram for a mammography scanning system 100, in accordance with one or more embodiments. Mammography scanning system 100 may operate by transmitting narrow RF-pulses at a certain pulse repetition frequency (PRF) in the form of rapid wideband (narrow width) sensor pulses at a chosen PRF in the 1-10 GHz band. The pulses can penetrate different types of biological tissue with varying attenuation constant. The sensor system 100 may, for example, transmit Gaussian pulses as short as a few pico-seconds wide with center frequency in the 1-10 GHz band. Mammography scanning system 100 may perform the required signal processing on the reflected response to construct a digitized representation of the subject or patient 105. In the receiver, amplitude and delay information may be extracted and digitally processed. As shown in the example of FIG. 1, the 3-6 GHz sensor is up-converted into the 57-64 GHz band.

Mammography scanning system 100 may include a number, N, of sensor transceivers, such as sensor transceiver 1000 illustrated in FIG. 1. N may be any number. For example, N may be 32×32=1024 miniature antenna elements for each of the sensor transceivers 1000 or N may be 512 for the embodiment shown in FIG. 3 having two 16×16 antenna arrays. System 100 may use an array of transceivers 1000 in which each transceiver is a single-chip sensor transceiver realized in complementary metal oxide semiconductor (CMOS) process that may reduce the cost, weight, and energy consumption of system 100 compared to multichip sensor transceiver implementations, may provide a set of completely isolated transceivers 1000 for system 100, may provide modularity of the system, and may facilitate extension of its application to medical diagnostic scanning.

Figure 3:
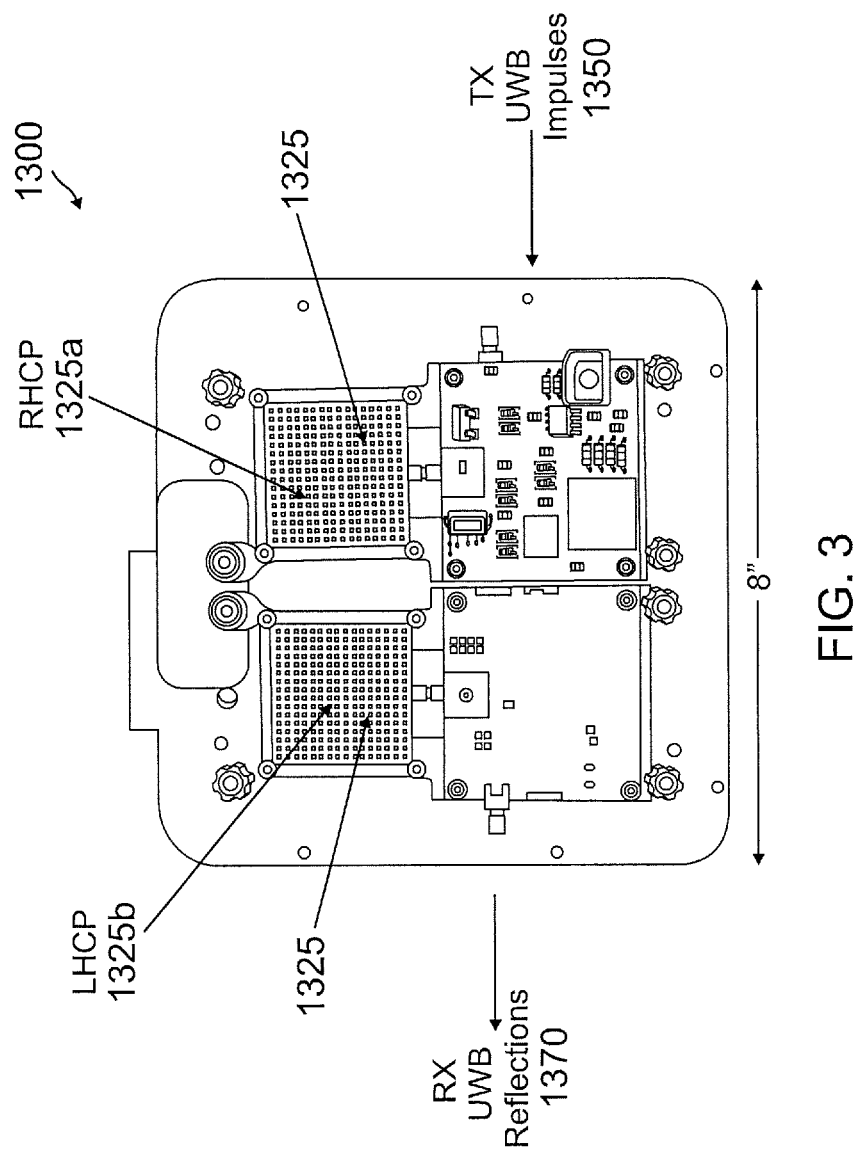
FIG. 3 is a perspective view illustrating an example of a physical layout for part of a sensor system, in accordance with an embodiment.

In one or more embodiments, the system 100 may employ either a linear (e.g., 1×n) or rectangular array (e.g., m×n, as seen in FIG. 3) including one or more sets of multiple single-chip sensor transceivers mounted on single low dielectric substrate printed circuit boards. In one embodiment, a multiple number of the single-chip sensor transceiver boards may be integrated to implement an N-channel linear array for rapid millimeter-wave scan of the subject 105. One of the transceivers may be used as a transmitter and all of the multiple (for each board) or N transceivers may be used as receivers. The transmitted pulse may be, for example, a first order Gaussian pulse with a center frequency of 4.35 GHz and a bandwidth greater than 2.5 GHz. The receivers may use a sampling on a continuous time binary value to achieve an equivalent sampling rate of 40 gigasamples per second (GS/s) or more.

Each transceiver 1000 may be connected via an Ethernet interface 1022 with a processor 130 that may, for example, perform processing that combines data from all transceivers 1000—whether in a rectangular array or a linear array that is moved to scan the scanning area—to provide an image, such as image 122, on a display 120. System 100 may also include a supervisor monitoring system 125 that may communicate with processor 130 via a network 126, as shown, which may include a private secure network, for example, or the Internet.

In system 100, an array of independent transceivers 1000 (using UWB sensor of primary processing unit 1020 as intermediate frequency (IF) and up- and down-converters of RF module 1010 in RF) may be used for near-field imaging. In FIG. 1, an arrangement with an integrated IF (sensor) board for each transceiver 1000 may operate at 1-10 GHz bandwidth. Results from a mathematical model of system 100 incorporating the inter-sample delay variations show that process variations are a strong influence on image degradation and a factor that is not easily rectified. In one or more embodiments, the problem of inter-sample delay variations may be addressed by direct calibration of the system 100 using one or more reflectors (also referred to as a calibration target) positioned at known locations in the image. FIG. 3 illustrates the arrangement of an integrated IF (radiometer) board operating at 3-6 GHz bandwidth up converted to 57-60 GHz side band. The measurement setup consists of a single transceiver mounted on two boards and angled independently to a focal length of 6 inches.

Figure 2:
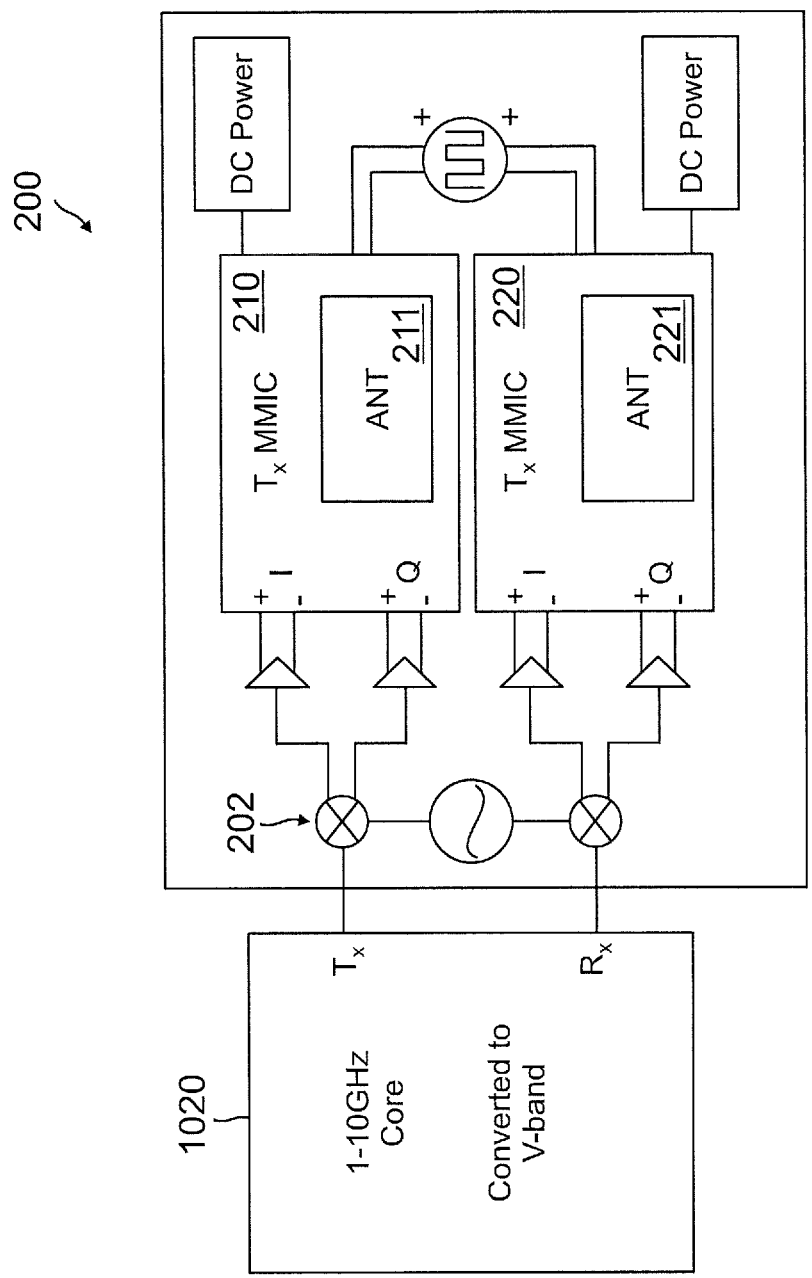
FIG. 2 is a system block diagram showing an example of an architecture of a phase measuring sensor array for a mammography scanning system in accordance with one embodiment.

FIG. 2 is a system block diagram showing an example architecture of a phase measuring sensor array 200 for a mammography scanning system 100 in accordance with one embodiment. As is shown in FIG. 2, the 1-10 GHz UWB core (base band) can be used as the sensor processing unit (e.g., processing unit 1020 as seen in FIG. 1). On the front-to-backend (FEB) the 1-10 GHz UWB core may be converted to in-phase and quadrature (I and Q) signals using an image rejection I/Q mixer 202. In this approach, a differntial, low noise and high frequency buffer can be used to create a differential base band (BB) type signal to preserve the signal to noise ratio for both I and Q. The gain is controlable both on the transmitter (Tx) 210 side and receiver (Rx) 220 side. Through a USB interface (not shown) both the frequecy of operation and also the gain can be programmed.

One advantage of the backscattering alignment (BSA) for a monostatic (e.g., transmitter and receiver are collocated) configuration, also called backscattering configuration, is that the transmitting antennas 211 and receiving antennas 221 are coordinated systems of the two antennas, such that the systems coincide. One reason to select this configuration is due to the fact that the majority of the existing polarimetric sensor systems operate with the same antenna for transmission and reception.

For single polarization systems, the scattered power is determined by means of the sensor's cross-section or the scattering coefficient. Nevertheless, a polarimetric sensor has to be considered as a multi channel system. Consequently, in order to determine the scattered power, it is necessary to consider all the data channels, that is, all the elements of the scattering matrix.

In one embodiment, arrays of right-hand circular polarization (RHCP) and left-hand circular polarization (LHCP) cannot identify the phase of a cluster cell (e.g., cancer cell). In an alternative embodiment, using the phase measurement provided by phase measuring sensor array 200, a method of signal processing is provided that can classify abnormal cell clusters by their detected phase differences. A deterministic relation between reflected power and phase of a "carrier-included" pulse form can be established, when reflected signals from a media encounter different dielectric constants. Furthermore, performance can be improved when utilizing polarized antennas. In such a scenario, a single transmitter can generate the polarized wave, and two receivers, in parallel, process the received signals at two different polarizations, leading to the necessity of two "identical" down converting hardware-paths (e.g., two parallel (but differently polarized) implementations of antenna 221, receiver 220, and receiver part of mixer 202) in the RX-block (only one receiver is shown in FIG. 2). The polarized receivers enable further characterization of different types of cancer cell clusters.

FIG. 3 is a perspective view illustrating an example of a physical layout for a radiometry sensor 1300 of a mammography scanning system, in accordance with an embodiment.

FIG. 3 shows an example of a sensor system 1300 that has been implemented using a UWB mm-wave radiometer technology operating with sub-200 picosecond (ps) bipolar pulses. As shown in FIG. 3, the sensor utilizes the unlicensed 3-6 GHz band, and up- and down-converted to 60 GHz (V-band). An adjustable PRF in the tens of MHz provides range resolution that is about 3 mm in free space. The received power can be digitally processed to extract relevant information on the reflecting object, e.g., patient body tissue or tumor.

FIG. 3 shows an example of left-hand circularly polarized (LHCP) and right-hand circularly polarized (RHCP) 16-by-16 element antenna arrays 1325 for a sensor system 1300. Although two antenna arrays 1325 are shown in FIG. 3, use of a circulator (not shown) as an isolator switch may enable use of a single antenna 1325 for both transmit and receive. In one embodiment, the transmit array 1325a and the receive array 1325b may be separately implemented as shown in FIG. 3.

Each active antenna array 1325 (LHCP and RHCP) may be implemented in a planar surface to provide higher signal resolution and phase contrast with minimal thickness of the arrays. LHCP and RHCP planar active array antennas 1325 may provide improved suppression of side lobes (e.g. achieving 20 dB suppression, for example) and may address a critical factor for clear sensor imaging as a result of antennas with high contrast efficiency (e.g., greater than 95%). As seen in FIG. 3, overall side dimension of a sensor unit with two antenna arrays may be no greater than 8 inches; thus, the side dimension of each planar active antenna array 1325 may be less than 4.0 inches. With formation of the beam occurring, in the spatial combining and power amplifier and low noise amplifiers, and use of LHCP and RHCP arrays cross coupling of a high power TX to RX input may be practically eliminated (e.g., greater than 20 dB suppression). As a result, in another implementation a high gain (42 dBi) 32×32 array 1325 can be used with 4.0 inch per side dimensions. Due to the dual use of antenna arrays 1325a and 1325b as combiner as well as beam former, the antenna module size can be substantially smaller, lighter, and easier to install than conventional sensors, especially for operation at the W-band.

Figure 4:
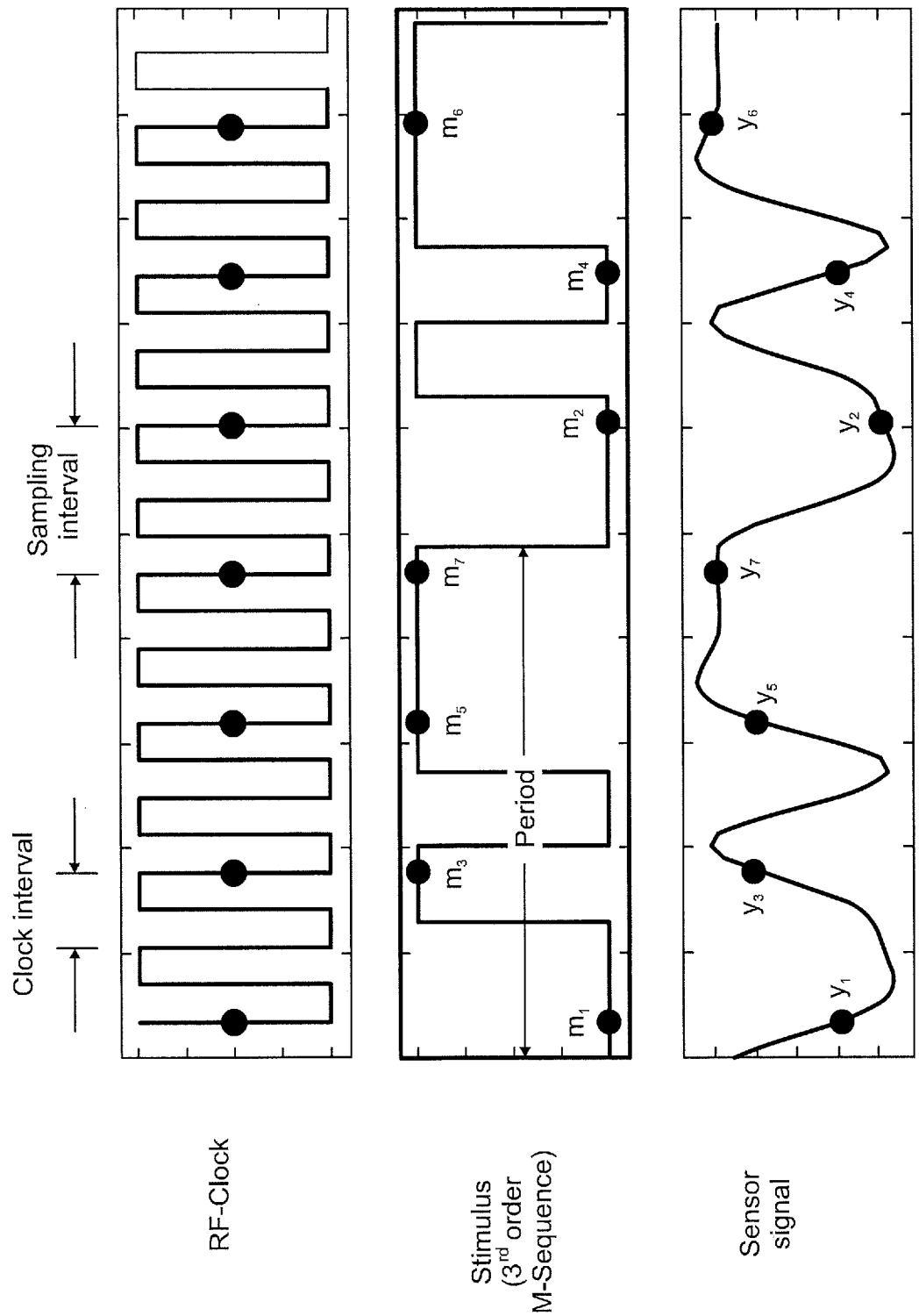
FIG. 4 is a set of timing diagrams for illustrating an example of signal coding for a mammography scanning system in accordance with one embodiment.
Figure 5:
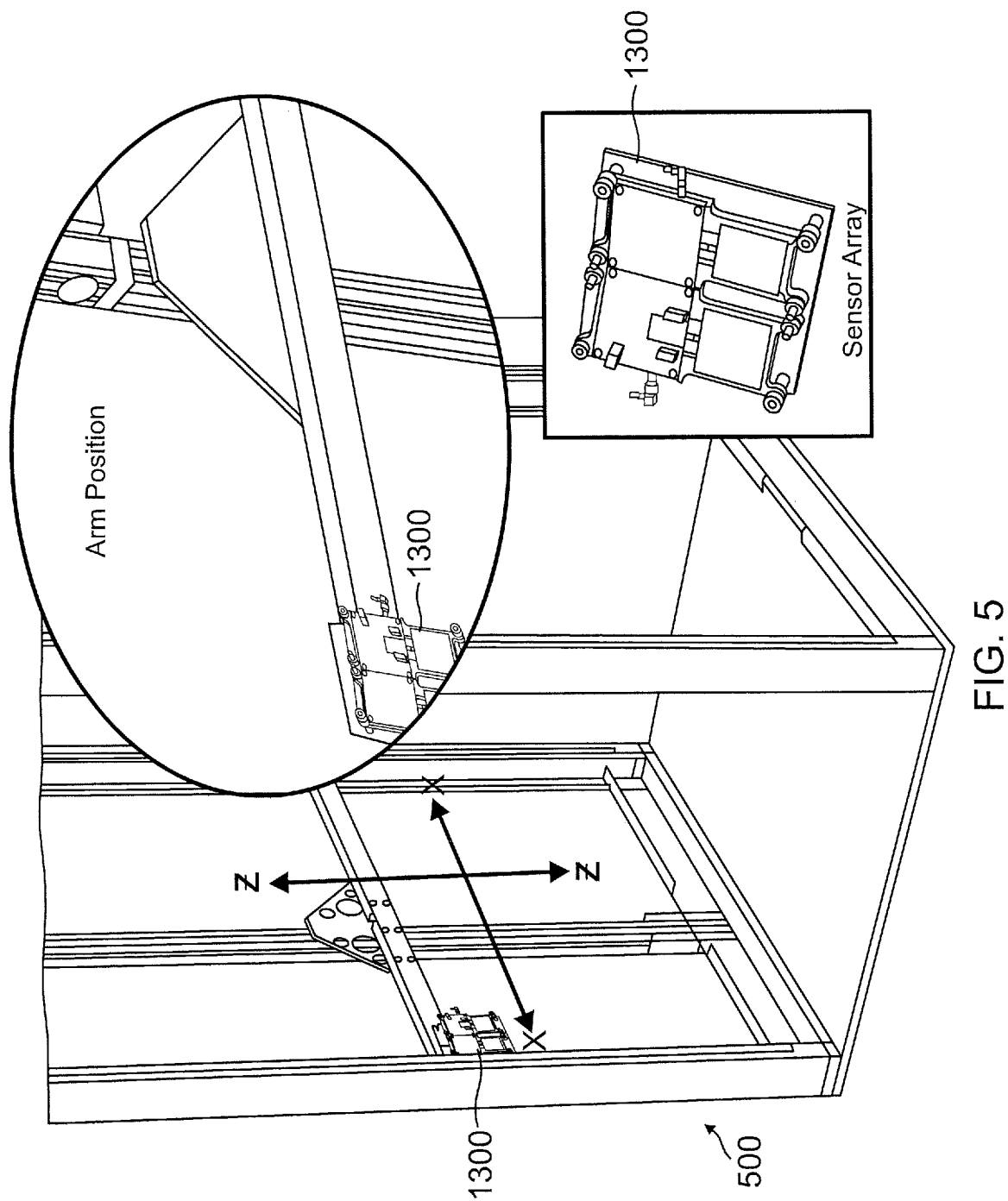
FIG. 5 is a perspective view diagram of an electromechanical scanning apparatus for linear scanning of a patient using a mammography scanning system in accordance with one embodiment.
Figure 6:
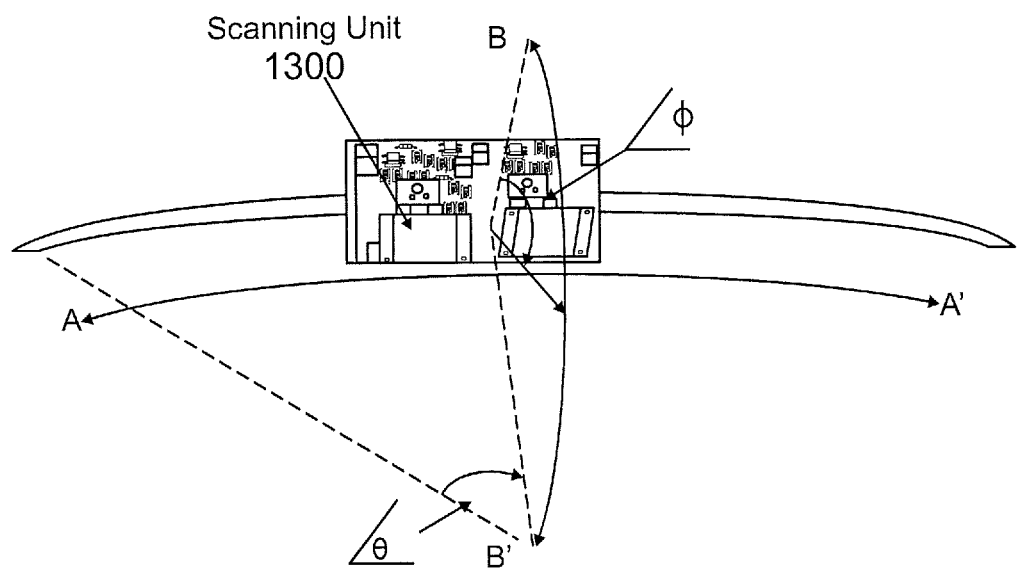
FIG. 6 is a perspective view diagram for an alternative scanning apparatus for radial scanning of a patient using a mammography scanning system in accordance with one embodiment.
Figure 7:
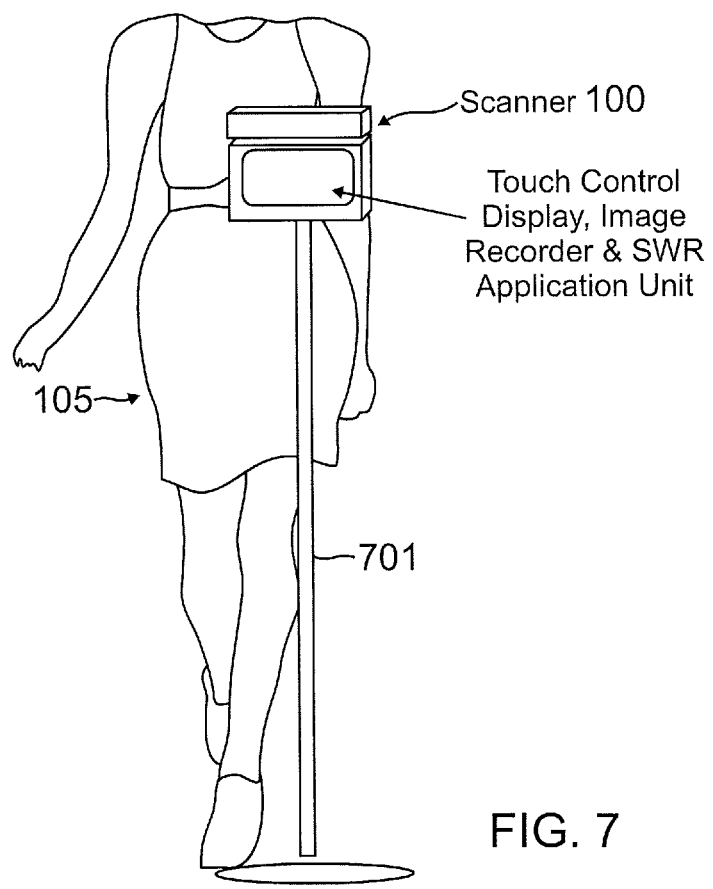
FIG. 7 is a perspective view diagram for an alternative scanning apparatus for handheld or portable scanning of a patient using a mammography scanning system in accordance with one embodiment.

FIG. 4 is a set of timing diagrams for illustrating an example of signal coding for a mammography scanning system 100 in accordance with one embodiment. The coding capability enables mammography scanning system 100 to mutually de-correlate signal exchange from adjacent scanner elements or reflections in the case of using an all-sensor implementation (e.g., as shown in FIGS. 6, 7) rather than a single Tx-Rx electro-mechanical scanner (e.g., as shown in FIG. 5). As an example, a Hadamard m-sequence coding may be chosen as the coding engine of choice.

The uppermost timing diagram of FIG. 4 shows a clock signal and clock interval (one cycle of the clock signal). A sampling interval (dots) is shown in relation to the clock signal. In this particular example, the sampling interval is twice as long as the clock interval for a sampling frequency (speed) half that of the clock frequency. The sampling speed may be varied in real-time during the signal reception. The middle timing diagram of FIG. 4 shows the timing for an m-sequence. Each element $m_i$ of the m-sequence may be referred to as a "chip" and helps to determine when a sample $y_i$ is taken from the sensor signal, e.g., reflected signal received from subject 105 by mammography sensing system 100 shown in FIG. 1, receiver 220 of FIG. 2, or sensor system 1300 of FIG. 3. An example of a sensor signal and samples $y_i$ corresponding to chips $m_i$ is shown in the lower most timing diagram of FIG. 4.

The data (e.g., samples $y_i$) capturing rate may be fixed to the lowest possible value which is equal to the clock rate of the sequence generator's shift register in this particular case. There are two consequences:

1) The amount of data per measured impulse response function corresponds to the theoretical minimum. The data throughput of the ultra-wideband sensor may be enormous. Therefore, any redundancy should be avoided during the data capturing.

2) Sampling with the suitable clock rate means that one has to take one data sample from every chip of the m-sequence. Since the m-sequence is periodic, one can distribute the data gathering over several periods which in turn results in relaxed speed requirements for the data capturing (sub-sampling) system. The sub-sampling can be controlled by a programmable binary divider.

For example, assuming a sampling rate of half the register clock rate, only every second chip is sampled. Within the first signal period (see the middle timing diagram of FIG. 4) these are the samples with an odd number and during the second period the samples with the even numbers are captured. In other words, after two periods, all data samples are captured without violation of the Nyquist theorem. The same holds for a dividing factor of e.g., 4, 8, requiring 4, respectively, 8 periods to capture the complete data set to calculate one impulse response function.

Commonly, either a frequency response or an impulse response function is of interest. The frequency response is acquired by Fourier Transform and the determination of the impulse response requires a time compression of the data. With respect to the latter, the desired impulse response function g(t) relates to the input and output signals by:

$$\psi_{ym}(\tau)=g(\tau)*\psi_{mm}(\tau) \quad (1)$$

where: $\psi_{mm}(\tau)$ is the auto-correlation of the transmit signal, $\psi_{ym}(\tau)$ is the cross correlation between receive and transmit signal and * symbolises convolution. If the bandwidth of the signal is large, $\psi_{mm}(\tau)$ is short compared to any variations in $g(\tau)$ and the equation may be simplified to $\psi_{ym}(\tau) \sim g(\tau)$ for $\psi_{mm}(\tau) \approx \delta(\tau)$. Hence, the input-output-correlation gives the wanted characteristic function of the measurement scenario. The cross-correlation is defined by:

$$\psi_{ym}(\tau)=\int y(t) \cdot m(t+\tau) dt \quad (2)$$

As long as the settling time is shorter than the period-length of the sequence-code, the result can be expressed by a matrix equation:

$$\begin{bmatrix} \psi_{ym,1} \\ \psi_{ym,2} \\ \psi_{ym,3} \\ \vdots \\ \psi_{ym,N} \end{bmatrix} = \begin{bmatrix} m_1 & m_2 & m_3 & \cdots & m_N \\ m_N & m_1 & m_2 & \cdots & m_{N-1} \\ m_{N-1} & m_N & m_1 & \cdots & m_{N-2} \\ \vdots & \vdots & \vdots & \ddots & \vdots \\ m_2 & m_3 & m_4 & \cdots & m_1 \end{bmatrix} \cdot \begin{bmatrix} y_1 \\ y_2 \\ y_3 \\ \vdots \\ y_N \end{bmatrix} \quad (3)$$

$$\psi_{ym} = M \cdot y \Box g$$

where:
$m=[m_1\ m_2\ m_3\ \ldots\ m_N]^T$ sampled data and $y=[y_1\ y_2\ y_3\ \ldots\ y_N]^T$. This equation represents a cyclic correlation in which the (N×N) matrix M is built from shifted versions of the digitised transmitter signal m. g is the digitised version of the impulse response function.

When incorporating the fact that the sequence is not fully random (periodic with m-sequence characteristics) the matrix M can be decomposed in a Hadamard matrix M=P·H·Q. Thus, the correlation is expressed as:

$$\psi_{ym}=P\cdot H\cdot Q\cdot y \qquad (4)$$

where H is the Hadamard matrix and P and Q are permutation matrices.

In summary, the options to the pre-processing DSP's, measurement data are:

Submit the captured data to a Fast Fourier Transform (FFT). This results in a complex spectrum roughly proportional to the frequency behavior of the transmission path.

Submit the captured data to a Fast Hadamard Transform (FHT). This leads to the impulse response which is based on the assumption of system stimulation by an ideal m-sequence.

Measure both stimulus and system reaction and calculate the actual cyclic cross-correlation. This leads to the impulse response.

Measure both stimulus and system reaction and calculate the complex cross-spectrum via FFT. The result is the frequency response function of the system.

An example of one ideal case is a beam forming system that positions the nulls at the point of reception of a cluster (e.g., tissue anomaly) reflection. The foregoing concerns, however, may be substantially reduced in the environment that the signal beam is directed at the breast vicinity. Hence, a high bandwidth of very short pulses at the V-band and W-band radio waves can penetrate tissue and resolve the tissue anomalies with high-resolution. As was mentioned, a millimeter-wave radio transmitter emits a train of very narrow pulses. The transiently radiated field impinges on tissues in its field of view and returns a reflected portion of that energy to a correlating receiver. Pseudo-random coding of the pulse train creates a signal that allows the correlating receiver to provide a processing gain that extracts very low energy reflected signals from background noise (coding gain). Similarly, the significant attenuation due to the penetration of RF waves at such high frequencies can be compensated for, or at least partially offset by, using the processing gain provided by the receiver, such as receiver 220 or the receive path of transceivers 1000 and processing units 1020.

In a typical RF imaging method, the radio moves along the target (see, e.g., FIG. 5) or rotates around it (see, e.g., FIG. 6) and scans the surface with a controlled beam width. However, a stationary and electronically steerable array antenna can scan the target with narrow beam width and at much higher speed (see, e.g., FIG. 7). As an example a set of radio transceivers would suffice to achieve a precision detection and location (range, angle, i.e., two-dimensional or 2-D) capability.

FIG. 5 is a perspective view diagram of an electromechanical scanning apparatus for linear scanning of a patient using a mammography scanning system 100 in accordance with one embodiment.

As shown in FIG. 5, one configuration of an electromechanical assembly system 500 for scanning a patient—who may, for example, stand inside electro-mechanical assembly system 500—is based on X-Z movement of a single sensor cell (e.g., radiometry sensor 1300 as seen in FIG. 3). The sensor 1300 electronics may operate at the V-band as has been described. The sensor 1300 can scan vertically (Z-Z direction) with 0.1 inch (1.5 mm) increments in the "Z" direction, which can reduce the breast scan time to less than 3 minutes.

In one embodiment, as a rapid linear horizontal scan (X-X direction) proceeds, the miniaturized Tx/Rx unit (e.g., sensor 1300 or sensor 200) scans the breast area vertically (Z-Z direction) facing the breast area from a certain angle and adjusts for angular error correction of the image.

FIG. 6 is a perspective view diagram for an alternative scanning apparatus for radial scanning of a patient using a mammography scanning system 100 in accordance with one embodiment.

As seen in an alternative example, shown in FIG. 6, the configuration of FIG. 6 allows a rapid scan of the breast area in real time and converts the result to an image that can be more accurate than that of the linear horizontal scan. The depicted radial scanner (FIG. 6) can remove the dispersion artifacts that can be observed in FIG. 9C and FIG. 10A and can provide much finer depth resolution. The example shown in FIG. 6 may provide a more robust solution, which takes advantage of a radial scan (A-A' direction) as shown in FIG. 6, and may reduce the scan time from a few minutes by a factor of ten to only a few seconds. The introduced complexity may be the dispersion error correction in the vertical (Z or angle B-B') direction.

In this scenario, the radiometer antenna (e.g., antenna of sensor unit 1300) scans on a semi-circular pattern (A-A' direction) around the target and senses from different angles (B-B' direction). This mode of operation gives a 2-D view of the object, e.g., the patient. In a practical scenario, a number of antennas (typically 16×16 or 32×32 antenna array) may be installed in the sensor's front-end to interrogate different angles. In general, the details observed in a circular (radial) scan compared to that of the linear scan can be vividly observed.

FIG. 7 is a perspective view diagram for an alternative scanning apparatus for handheld or portable scanning of a patient using a mammography scanning system 100 in accordance with one embodiment. The system 100 may be simply placed on a stand 701 that can have integrated processing and display control unit for ease of operation and portability as shown in FIG. 7. In this configuration, mammography scanning system 100 may employ the beam forming techniques developed specifically for wafer scale antenna arrays, described above, along with beam steering techniques to implement a stationary and electronically steerable array antenna that can scan the target (e.g., patient 105) with narrow beam width and at much higher speed than a mechanically based scan requiring movement of the sensor.

Figure 8A:
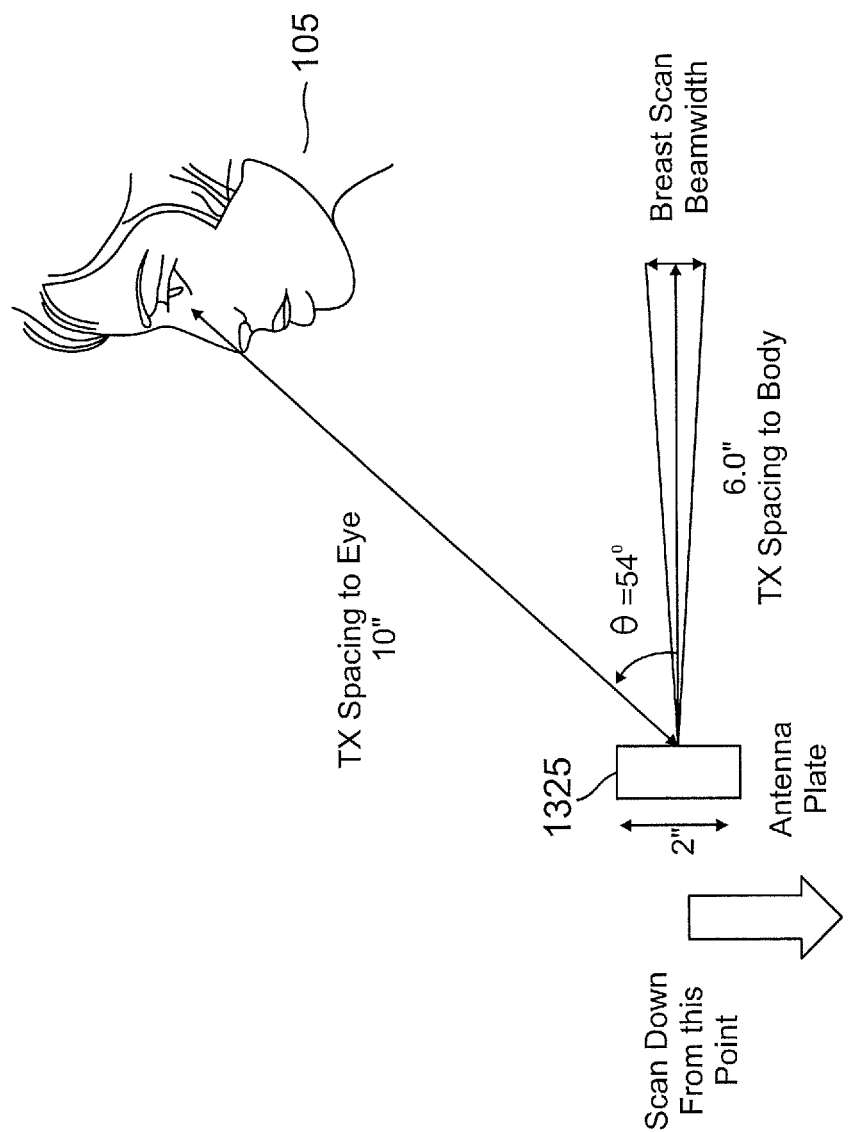
FIG. 8A is a schematic diagram illustrating an example of safety considerations for scanning a patient using a mammography scanning system in accordance with one embodiment.
Figure 8B:
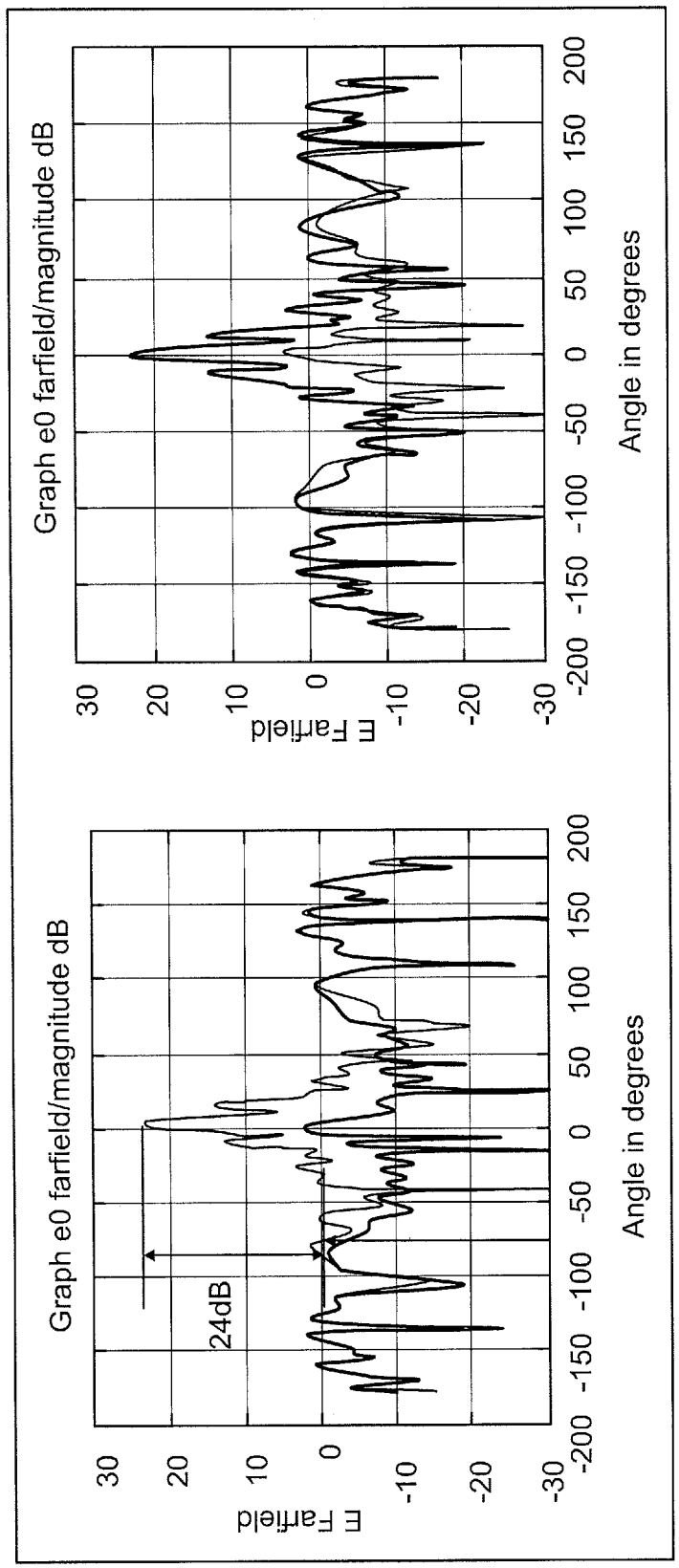
FIG. 8B is a set of graphs showing co-polarization and cross polarization radiation patterns for wafer scale, LHCP and RHCP antenna arrays for a mammography scanning system, illustrating the safety considerations shown in FIG. 8A, in accordance with an embodiment.

FIG. 8A is a schematic diagram illustrating an example of safety considerations for scanning a patient using a mammography scanning system 100 in accordance with one embodiment. FIG. 8B is a set of graphs showing co-polarization and cross polarization radiation patterns for wafer scale, LHCP and RHCP antenna arrays for a mammography scanning system, illustrating the safety considerations shown in FIG. 8A, in accordance with an embodiment.

Mammography scanning system 100 may be implemented in embodiments that address the impact of transmit power on ultra sensitive parts of body to ensure that complete safety of the person (patient 105) under screening is addressed based on published data. Published data is available, for example, from an investigation of acute ocular injury threshold at 76 GHz band by prolonged exposure of rabbits' eyes. In the investigation, pigmented rabbits were exposed unilaterally to 200, 100, 75, 50, 10 mW/cm² at 76 GHz band millimeter wave for 6 minutes with a lens antenna. Corneal opacity, epithelial injury, miosis (excessive constriction of the pupil of the eye), and ocular inflammation were present up to 2-3 days after exposure at a dose of 200 mW/cm². No ocular changes other than reversible corneal epithelial injury were seen following exposure at 100 and 75 mW/cm². There were no ocular changes after exposure at doses of 50 or 10 mW/cm². Six-minute exposure to 76 GHz 10 mW/cm² did not induce any detectable ocular tissue damage based on the experiments. This is an equivalent energy of about 2.5 mW (per pupil)×360 sec=900 mJ or 0.9 Joule.

In one embodiment, such as that illustrated in FIG. 5, the UWB transmitter scan rate is approximately 8 in./sec for 180 seconds (0.1 in. increments for an 8 in. scan width) focused on the breast area and away from the eyes by 10 in. before each scan (see FIG. 8A) and 25 in. at the end of each scan. FIG. 8B illustrates the transmission pattern of the 16×16 RHCP and LHCP arrays shown in FIG. 3 and FIG. 8A. As shown in FIG. 8A, at the beginning of the scan, antenna array 1325 should be at least 6 in. from the breast area and 10 in. from the eye of patient 105, and the angle θ of transmitter array 1325 away from the eye of patient 105 is about 54 degrees. For the UWB transmitter the field strength emission limits (in free space) can be expressed in terms of an effective isotropic radiated power (EIRP) level, using the equation: EIRP=$E_0$+20 $\log_{10}$ D−104.8, where: EIRP=EIRP corresponding to the electric field strength $E_0$ (dBμV/m) and D=reference measurement distance (meters).

Based on transmitter propagation pattern of −24 dB suppression at 54 degrees away from the center of array 1325 (see FIG. 8B), the peak power of received signal to the eye, as seen in FIG. 8A, is 3 nano-watts, and power density is 0.3 nano-watts/cm² or 100,000,000 less than the safe exposure limit. Based on this power density and exposure time of 180 seconds for the entire scan from the starting point to the end, the total energy delivered to the retina is about 11 nano Joules (ηJ). The amount of energy delivered to one eye is 1,000,000,000 times less than the safe test limits observed with the laboratory rabbits. Similarly, the power density delivered to the breast area is about 0.3 mW/cm² (see FIG. 8B) which is about 100 times less than the safety personnel limit of using electronics devices by the US Department of Defense (Appendix A; radiation hazards to personnel from DoD ISNT 6055.11 of the RADHAZ document).

FIG. 9 comprises three perspective views A, B, and C, showing, at A, a plan view of a phantom, or test model of cancerous body tissue; at B, a profile view of the phantom in operational relationship to a scanning sensor of a mammography scanning system; and at C, a display image of radiometry scan of the phantom produced by a mammography scanning system 100, each in accordance with one embodiment.

A set of phantoms (models of body tissue that simulate the reaction of sensor energy with actual body tissue) were prepared based on the composition of various ingredients which closely represents the behavior of the breast tissue at the 60 GHz radiometry of mammography scanning system 100. For example, the composition of the mix to build such a semisolid skin-equivalent phantom 901 may include: deionized water; agar; polyethylene powder (PEP); TX-151; and sodium azide, NaN3. Water is the main constituent of the phantom because it is also the main skin tissue component. It primarily determines the dispersive behavior of the phantom. Agar is employed for the retention of self-shaping, and its contribution to the phantom dielectric properties is negligible. Polyethylene powder (PEP) is used to tune the real and imaginary parts of the phantom permittivity. TX-151 increases the viscosity since the agar and polyethylene powder cannot be mixed directly, and sodium azide serves as a preservative.

Fabrication of phantoms and image reconstruction has been used to test mammography scanning system 100. Images were created by scanning impulses with picosecond (ps) pulse width as a source (3-6 GHz UWB base band) and measuring the reflected waves (57-60 GHz band) from discontinuous layers of dielectric constant in the phantoms, as shown at B in FIG. 9. Since the transmitted pulse is distorted due to the limiting bandwidth of antennas, wideband and non-dispersive antennas were used for the measurement.

The transmitted power from IF was about −13 dBm, the RF transmitted power was less than 50 mW and the beam width of the Tx-Rx antennas were about 4 degrees. RF operating frequency was from 57 to 60 GHz. A polyurethane mold was prepared to simulate the average breast size and depth, as shown at A and B in FIG. 9. Three reflective objects 902, with different shapes and sizes, were placed at the surface (simulating the breast interior) of phantom 901 as shown at A in FIG. 9.

The image constructed from the 60 GHz scanner is shown at C in FIG. 9:

a) top-right 903a: 15 mm oval at 20 mm depth, scan angle=90 (perpendicular and directive);

b) middle-left 903b: 10 mm circular at 15 mm depth, scan angle=90 (perpendicular and directive);

c) bottom-middle 903c: 20 mm rectangle at 40 mm depth, scan angle=90 (perpendicular and directive)

The constructed image, shown at C in FIG. 9, demonstrates the strength of signal (sensitivity) with respect to the size and placement of the reflectors 902. A 20 mm rectangle shape reflector at the depth of 40 mm is detected, while highest intensity is from a 15 mm oval reflector at the 20 mm depth.

Figure 10:
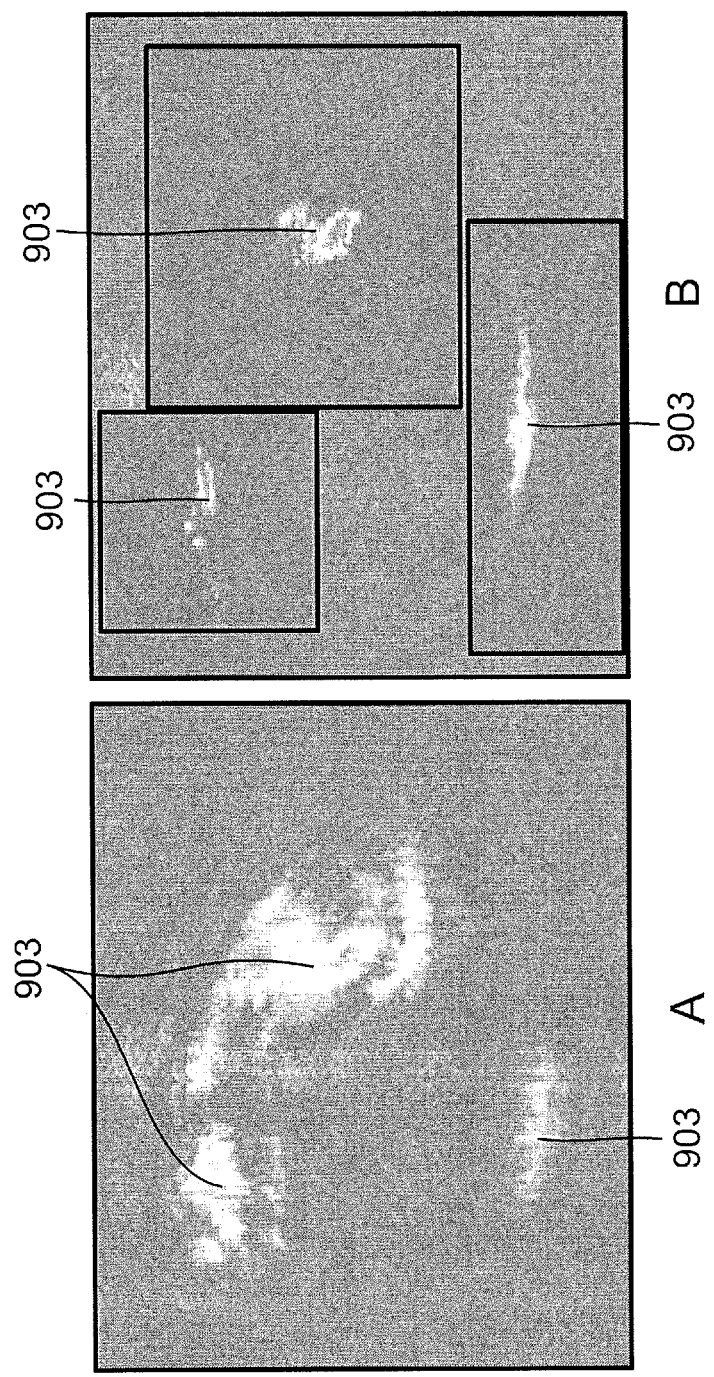
FIG. 10 comprises two image displays, A and B, for comparison, of a radiometry scan of the phantom as shown in FIG. 9 and produced by a mammography scanning system, each in accordance with an embodiment.

FIG. 10 comprises two image displays, A and B, for comparison, of a radiometry scan of the phantom as shown in FIG. 9 and produced by a mammography scanning system 100, each in accordance with an embodiment. The display at A in FIG. 10 is the same as the display at C in FIG. 9 and is repeated for direct comparison to the display at B in FIG. 10.

Further digital processing can be performed on the image of A in FIG. 10 to present the cluster (anomalous tissues) edges more clearly. By arranging edge detection filters from the received reflected power, the detected clusters can be further refined as shown at B in FIG. 10. A finer beam width and correction to the curvature of the breast by scanning the breast in a conformal pattern (e.g., semi-circular manner) may be implemented to enhance the imaging based on hardware modification. It should be noted that mammography system 100 is capable of scanning the breast nonintrusively and through clothing.

Figure 11:
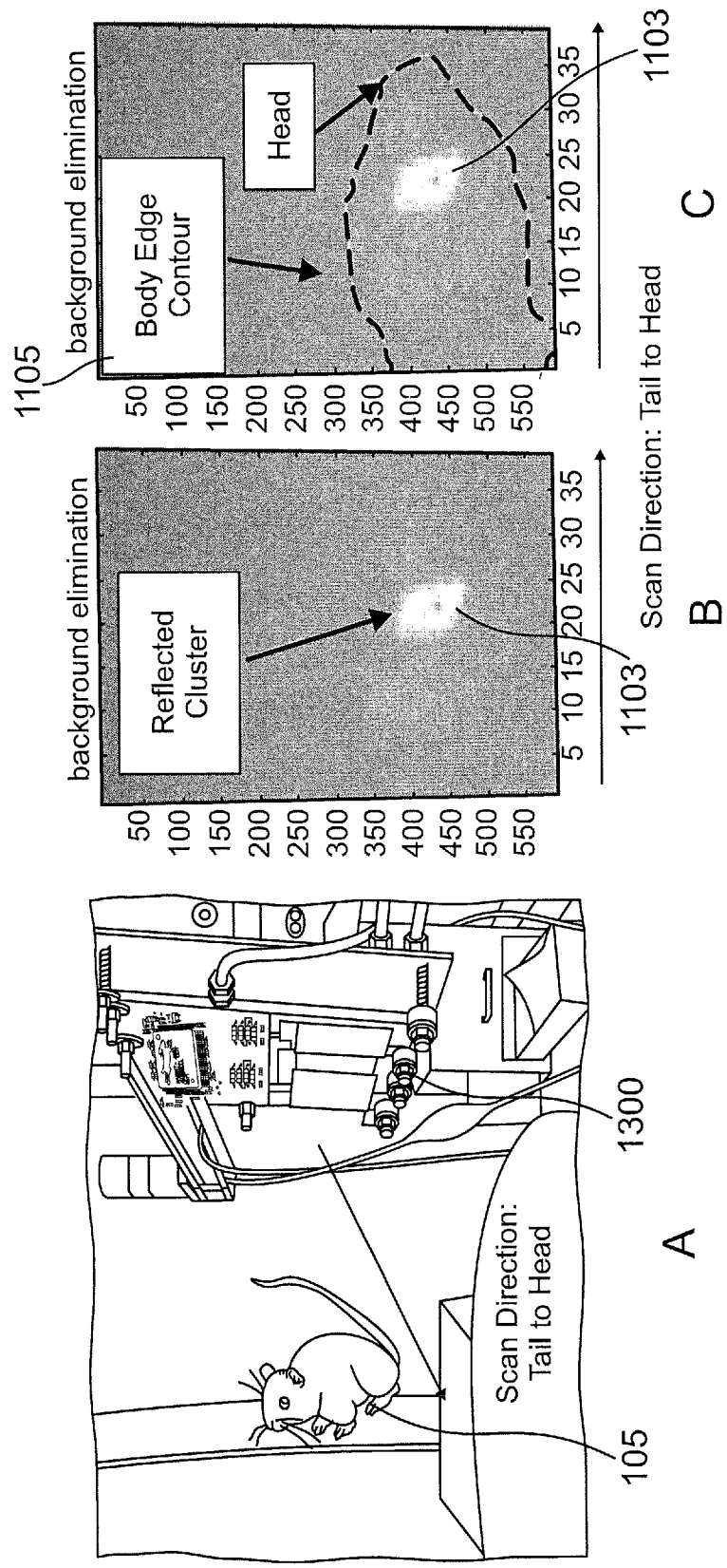
FIG. 11 comprises three perspective views A, B, and C, showing an experimental setup and images generated using a mammography scanning system in accordance with one embodiment.

FIG. 11 shows an experimental setup and images generated using a mammography scanning system 100 in accordance with one embodiment. A test subject 105 (lab mouse) was scanned using a sensor 1300 as shown at A in FIG. 11. FIG. 11 at B shows an image 1103, generated by mammography scanning system 100 of anomalous tissue present in test subject 105. FIG. 11 at B shows differentiation of certain tissues from the rest. For example, the outline of the mouse body edge contour 1105 and head shape can be differentiated from the anomalous tissue image 1103. FIG. 11 illustrates the value of pseudo-random coding (e.g., Hadamard coding) of the pulse train that creates a signal and allows the correlating receiver to extract very low energy reflected signals from background noise (e.g., coding gain). This and similar coding techniques provide significant processing gain that is essential for the large attenuation of transmitted signals in a breast operating at this high frequencies in producing the clearer images seen at C in FIG. 11. Furthermore, when multiple sensors scan the breast, the cross channel suppression significantly (20-30 dB) reduces the clutter associated from neighboring channels.

Figure 12A:
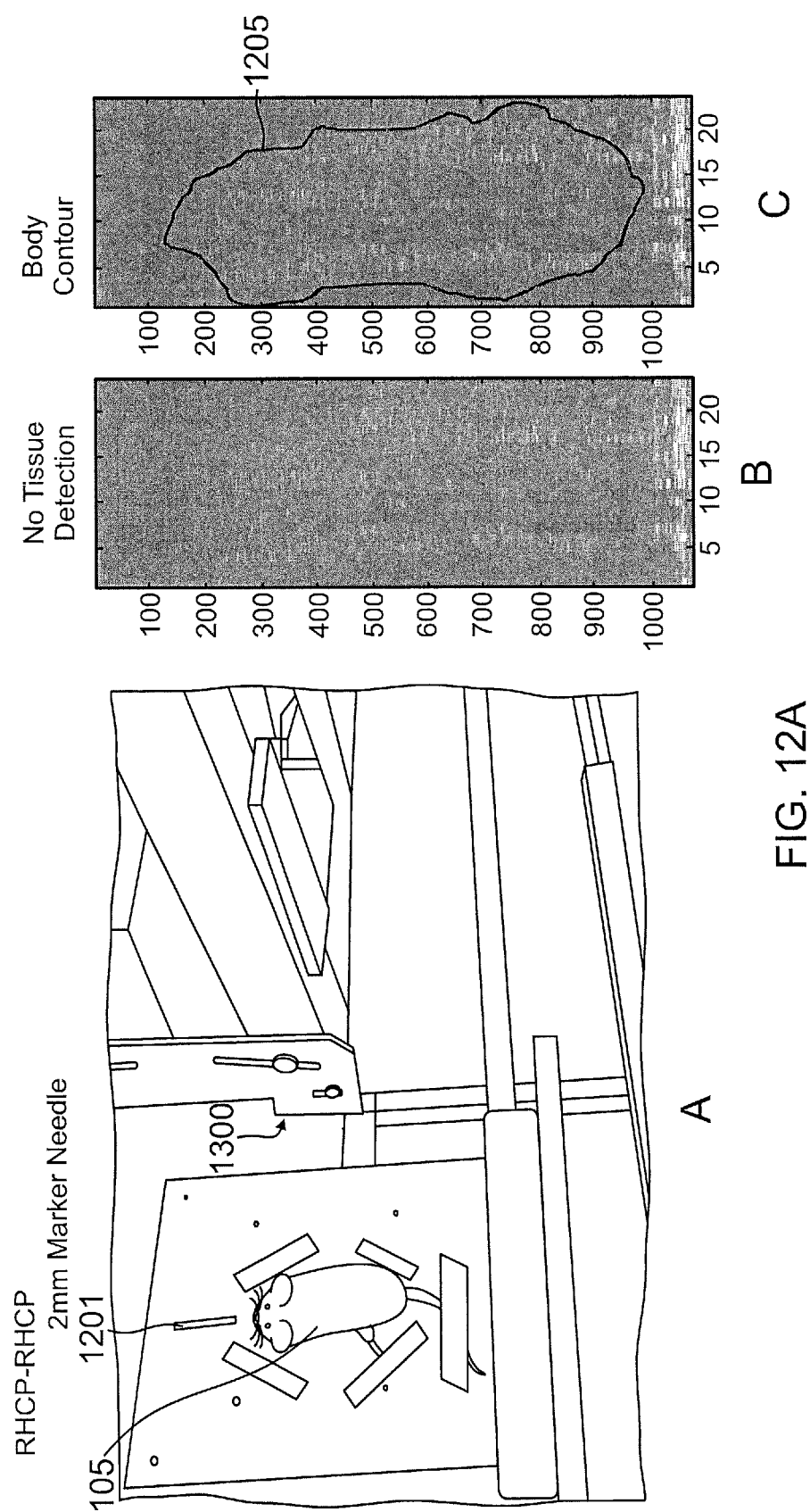
FIG. 12A comprises three perspective views A, B, and C, showing an experimental setup and images generated using right hand circularly polarized (RHCP) transmission and RHCP reception by a mammography scanning system in accordance with one embodiment.

FIG. 12A shows an experimental setup and images generated using right hand circularly polarized (RHCP) transmission and RHCP reception (same polarization for both) by a mammography scanning system 100 in accordance with one embodiment.

A more realistic test was performed, as shown at A in FIG. 12A, on a test subject mouse 105 with lymphoma cancer around its neck. A 2 mm diameter marker needle 1201 was included in the scan. As shown at B and C in FIG. 12A, are scanned regions of the mouse's body. Transmitted power was kept at the minimum to simulate a worst case condition test. The cancer cluster 1205 at the neck area was detected in multiple angles of scan. Since no pathology service was available at the time, it is suspected that the cancer was lymphoma. An important observation is the differentiation of the cancerous cell cluster from the other tissues of the mouse's body and skeleton. The marker needle 1201 did not show up in the scan images.

Figure 12B:
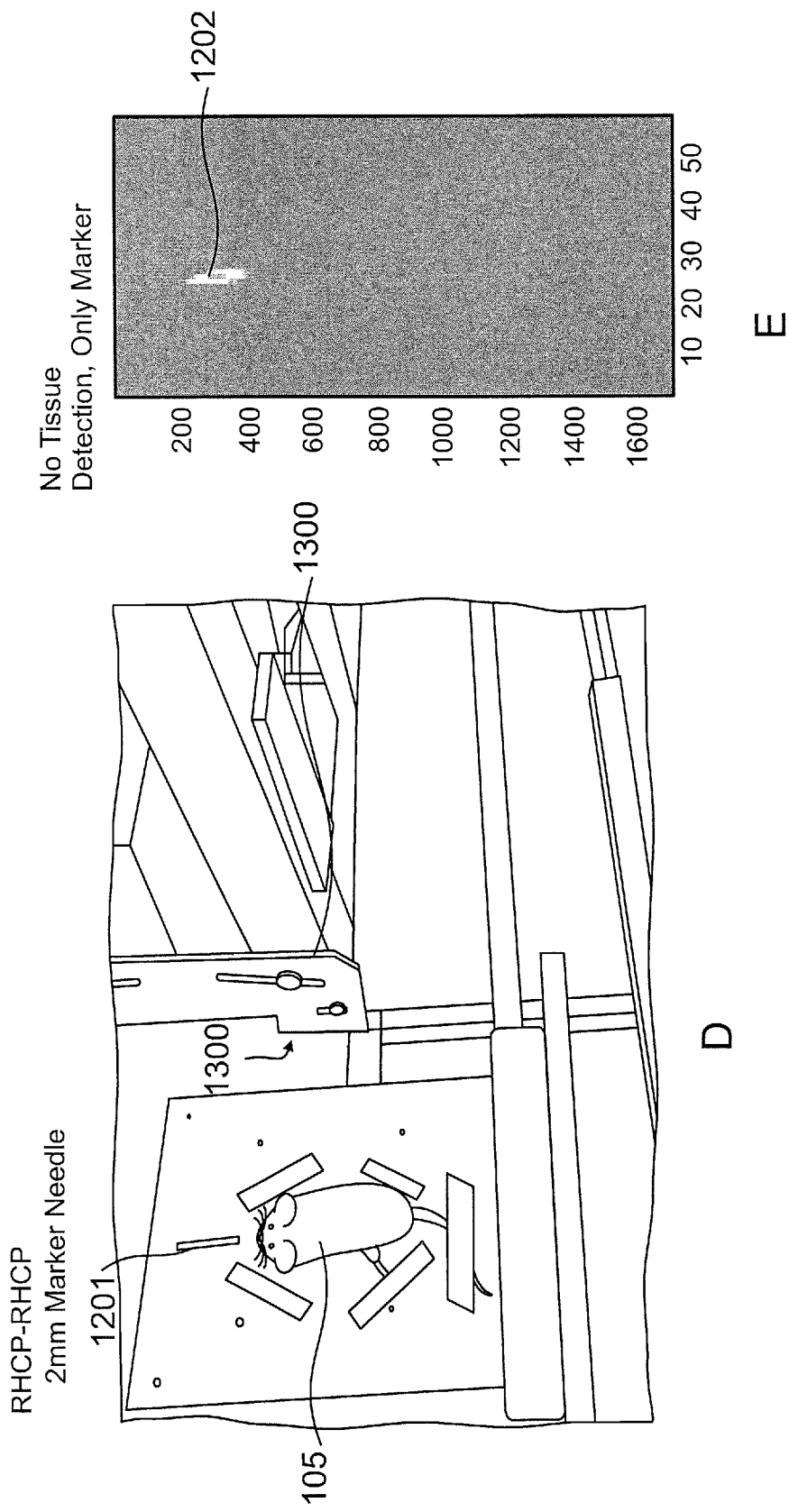
FIG. 12B comprises two perspective views D and E, showing the experimental setup and images generated using left hand circularly polarized (LHCP) transmission and RHCP reception (or vice versa) by a mammography scanning system in accordance with one embodiment.

FIG. 12B shows the experimental setup and images generated using left hand circularly polarized (LHCP) transmission and RHCP reception (or vice versa, different polarizations) by a mammography scanning system 100 in accordance with one embodiment.

A scan using different polarizations for transmit and receive was performed as shown at D in FIG. 12B, on a test subject mouse 105 with lymphoma cancer around its neck. A 2 mm diameter marker needle 1201 was included in the scan. As shown at E in FIG. 12B, are scanned regions of the mouse's body. Transmitted power was kept at the minimum to simulate a worst case condition test. The marker needle 1201 now shows up as image 1202 in the scan image.

As disclosed above with reference to FIG. 2, implementation of an array of right-hand circular polarization (RHCP) and left-hand circular polarization (LHCP) arrays can be used to identify the phase of an object in the case that the array is used as part of a scanner transmitter and receiver to significantly improve detection of anomalous tissues and other features of the scanned subject 105.

Embodiments described herein illustrate but do not limit the disclosure. It should also be understood that numerous modifications and variations are possible in accordance with the principles of the present disclosure. Accordingly, the scope of the disclosure is best defined only by the following claims.

What is claimed is:

1. A mammography scanning system comprising:
a first antenna array configured to transmit an ultra wide band (UWB) sensor signal using right-hand circular polarization;
a second antenna array configured to receive a reflection of the UWB sensor signal using left-hand circular polarization;
a transmitter configured to provide a pseudo-random coding to the UWB sensor signal; and
a correlating receiver in communication with the second antenna array and configured to use the pseudo-random coding of the UWB sensor signal to provide a processing gain to extract the reflection of the UWB sensor signal from background noise.

2. The system of claim 1, further comprising:
a converter configured to convert a base band signal of the UWB sensor signal to in-phase and quadrature (I and Q) signals to provide a phase measurement at the correlating receiver; and
a signal processor configured to use the phase measurement to classify a plurality of abnormal cell clusters by their detected phase differences.

3. The system of claim 1, wherein:
the pseudo-random coding is a Hadamard coding; and
first antenna array is a stationary and electronically steerable array antenna.

4. The system of claim 1, further comprising:
a first sensor using a first Hadamard coding of a first UWB sensor signal to scan a subject on a first channel;
a second sensor using a second Hadamard coding of a second UWB sensor signal to scan the subject on a second channel; and
a processor configured to provide cross channel suppression, using the Hadamard coding, to process an image of the subject.

5. The system of claim 1, wherein the UWB sensor signal is a radio frequency (RF) signal that has a frequency in the V-band or the W-band and a bandwidth of at least 3 GHz.

6. The system of claim 1, wherein the scanning system is handheld and moved in a radial scan around a subject.

7. A mammography scanning system comprising:
a first antenna array configured to transmit and receive a V-band ultra wide band (UWB) sensor signal having left-hand circular polarization;
a second antenna array configured to receive the UWB sensor signal with right-hand circular polarization;
a transmitter configured to provide a pseudo-random coding to the UWB sensor signal; and
a correlating receiver in communication with the second antenna array and configured to use the pseudo-random coding of the UWB sensor signal to provide a processing gain to extract reflected signals from background noise.

* * * * *